(12) United States Patent
Vaidya et al.

(10) Patent No.: US 7,808,632 B2
(45) Date of Patent: Oct. 5, 2010

(54) NANOCOMPOSITE MATERIAL FOR DIRECT SPECTROSCOPIC DETECTION OF CHEMICAL VAPORS

(75) Inventors: Bikas Vaidya, College Station, TX (US); Ulf Werner Drechsler, Bryan, TX (US)

(73) Assignee: Lynntech, Inc., College Station, TX (US)

( * ) Notice: Subject to any disclaimer, the term of this patent is extended or adjusted under 35 U.S.C. 154(b) by 580 days.

(21) Appl. No.: 11/768,040

(22) Filed: Jun. 25, 2007

(65) Prior Publication Data
US 2008/0278708 A1  Nov. 13, 2008

Related U.S. Application Data

(60) Provisional application No. 60/820,522, filed on Jul. 27, 2006.

(51) Int. Cl.
*G01J 3/28* (2006.01)
(52) U.S. Cl. ................................ 356/300
(58) Field of Classification Search ......... 356/244–246, 356/300–301, 445
See application file for complete search history.

(56) References Cited

U.S. PATENT DOCUMENTS

| | | | |
|---|---|---|---|
| 6,649,416 | B1 | 11/2003 | Kauer et al. |
| 6,985,818 | B1 | 1/2006 | Samuels |
| 2003/0032039 | A1* | 2/2003 | Cunningham et al. ....... 356/320 |
| 2003/0231304 | A1* | 12/2003 | Chan et al. ................ 356/301 |
| 2006/0141466 | A1* | 6/2006 | Pinet et al. ................ 356/319 |
| 2006/0263257 | A1 | 11/2006 | Beauchamp et al. | |

FOREIGN PATENT DOCUMENTS

WO  WO 0241043  5/2002

OTHER PUBLICATIONS

Rosa Leon, Richard Noetzel, Simon Fafard, Diana Huffaker; Semiconductor Quantum Dots II; Materials Research Society Symposium Proceedings vol. 642; Nov. 27-30, 2000; 8 pages; Boston, Massachusetts.

(Continued)

*Primary Examiner*—Kara E Geisel
(74) *Attorney, Agent, or Firm*—Jeffrey L. Streets; Streets & Steele

(57) ABSTRACT

Method and material for spectroscopic detection of organic chemicals. The material is a substantially optically transparent solid, such as ZnS, having a high surface area for adsorption of an analyte, such as organic chemical vapors. The solid material preferably has metal nanoparticles, such as gold, silver or copper nanoparticles, deposited on the surface for signal enhancement. A template compound, such as cetyl trimethyl ammonium bromide and alkoxylate block polymers, may be used during the material synthesis, such as reacting zinc chloride and sodium sulfide in the presence of the template compound, and later removed through calcination and washing to achieve the high surface area. The method of use includes collecting an analyte on the material and detecting the spectroscopic response of the analyte while it is collected on the surface. The mechanism of collection may include adsorbing, absorbing, and preconcentrating. Preferably, the spectroscopic response is selected from infrared spectra or ultraviolet-visible spectra.

30 Claims, 12 Drawing Sheets

OTHER PUBLICATIONS

Alexander Cartwright, Thomas M. Cooper, Shashi P. Karna, Hachiro Nakanishi, Organic and Nanocomposite Optical Materials; Materials Research Society Symposium Proceedings vol. 846; Nov. 28-Dec. 3, 2004; 7 pages; Boston, Massachusetts.

Michael J. Sailor, Eric J. Lee; Surface Chemistry of Luminescent Silicon Nanocyrstallites; 11 pages, Advanced Materials, 1997, vol. 9, No. 10.

Partial International Search Report, PCT/US2007/074591, Feb. 15, 2008.

Masatoshi Osawa, Surface-Enhanced Infrared Absorption, 2001, 25 pages, Catalysis Research Center, Hokkaido University.

R. Kellner, B. Mizaikoff, M. Jakusch, H.D. Wanzenbock and N. Weissenbacher, Surface-Enhanced Vibration Spectroscopy: A New Tool in Chemical Sensing?, 1997, 9 pages, vol. 51, No. 4, Vienna, Austria.

Richardo F. Aroca and Daniel J. Ross, Surface-Enhanced Infrared Spectroscopy, 2004, 15 pages, University of Windsor, vol. 58, No. 11, Madrid, Spain.

Tuan Vo-Dinh, Surface-enhanced Raman spectroscopy using metallic nanostructures, Advanced Monitoring Development Group, Life Science Division, Oak Ridge National Laboratory, 1998, 26 pages, vol. 17, No. 8&9, Oak Ridge, Tennessee.

Alan Campion and Patanjali Kambhampati, Surface-enhanced Raman scattering, 1998, 10 pages, vol. 27, Department of Chemistry and Biochemistry, The University of Texas, Austin, Texas.

Shuming Nie and Steven R. Emory, Probing Single Molecules and Single Nanoparticles by Surface-Enhanced Raman Scattering, www.sciencemag.org, Feb. 21, 1997, 5 pages, vol. 275, Indiana.

John Assulf Tornes, Aase Mari Opstad and Bjorn Arne Johnsen, Use of Solid-Phase Extraction in Determination of Chemical Warfare Agents, Mar. 22, 1991, 17 pages, Part I, Norwegian Defence Research Establishment, Division of Environmental Toxicology, Kjeller, Norway.

John Assulf Tornes, Aase Mari Opstad and Bjorn Arne Johnsen, Use of Solid-Phase Extraction in Determination of Chemical Warfare Agents, Mar. 22, 1991, 5 pages, Part II, Norwegian Defence Research Establishment, Division of Environmental Toxicology, Kjeller, Norway.

Jianquan Li, Henri Kessler, Michel Soulard, Lachen Khouchaf and Marie-Helene Tuiller, Nanosized Zinc Sulfide Obtained in the Presence of Cationic Surfactants, 1996, 4 pages, France.

W. Hertl, Surface Chemical Properties of Zinc Sulfide, Nov. 12, 1987, 5 pages, Research & Development Division, Corning Glass Works, Corning, New York.

Encai Hao, Ryan C. Bailey, George C. Schatz, Joseph T. Hupp and Shuyou Li, Synthesis and Optical Properties of "Branched" Gold Nanocrystals, Published on web Jan. 9, 2007, 4 pages, vol. 4, No. 2, Department of Chemistry, Northwestern University, Evanston, Illinois.

J.J. Mock, A. Barbic, D.R. Smith, D.A. Schultz, and S. Schultz, Shape effect in Plasmon resonance of individual colloidal silver nanoparticles, Jan. 29, 2002, 5 pages, vol. 116, No. 15, Department of Physics, University of California, San Diego, La Jolla, California.

* cited by examiner

NANOCOMPOSITE MATERIAL FOR DIRECT SPECTROSCOPIC DETECTION OF CHEMICAL VAPORS

This application claims priority from U.S. provisional patent application 60/820,522 filed on Jul. 27, 2006.

BACKGROUND OF THE INVENTION

1. Field of the Invention

The presenting invention relates to materials, detectors and systems for spectroscopic detection.

2. Background of the Related Art

The identification of chemical vapors requires both collection and analysis of the vapors. The collection technique must obtain the chemical vapor and provide the chemical in a form that is convenient for analysis. The analysis technique must be able to utilize the chemical and provide the desired identification information. For example, trace amounts of chemical warfare agents have been successfully detected using solid phase extraction (SPE) techniques followed by gas chromatography-mass spectrometry (GC-MS) analysis. However, this method is complicated, as it requires very sophisticated and expensive instrumentation and highly skilled operator to perform the test.

Optical spectroscopic methods such as infrared and Raman spectroscopy can provide unique spectral fingerprints of organic compounds, facilitating the unambiguous identification of chemical warfare agents (CWAs) and other toxic industrial chemicals. However, improved collections techniques are necessary before these analytical techniques can be used to full advantage.

While solid phase extraction substrates can be used to collect chemical vapors, substrates known to be capable of adsorbing chemical vapors are also known to interfere with spectroscopic detection. In other words, the solid phase extraction substrate that collects and concentrates organic vapors onto its surface is not "spectroscopically benign." A substrate is spectroscopically benign if it either transmits or reflects electromagnetic radiation over a desired range of wavelengths.

Therefore, detecting trace concentrations of a chemical analyte, such as an organic vapor, remains a challenge and there is a need for more sensitive and selective chemical and biological sensor technologies. It would be desirable if a sensor could collect and analyze chemical analyte samples without extensive handling or processing of the sample. It would be further desirable if the sensor provided efficient collection and sensitive analysis to enable detection of even small amounts of an analyte. Still, it would be even more desirable if the sensor could identify or differentiate a chemical of interest from a mixture of other chemicals.

SUMMARY OF THE INVENTION

The present invention provides a method of spectroscopic detection comprising the steps of collecting at least one analyte onto a solid material comprising a surface of a substantially optically transparent material with gold, silver or copper nanoparticles deposited on the surface, and detecting the spectroscopic response of the at least one analyte while it is collected on the surface. A preferred substantially optically transparent material is zinc sulfide. The step of collecting may include preconcentrating the at least one analyte on the surface of the material, which preferably has a surface area density of about 100 square meters per gram or higher. The method may further comprise identifying the presence of an organic compound of interest in the at least one analyte comprising a mixture of other organic chemicals. Preferably, the spectroscopic response is selected from infrared spectra or ultraviolet-visible spectra. Specific examples of suitable spectroscopic responses include diffuse reflectance Fourier transform infrared spectroscopy and attenuated total reflection infrared spectroscopy. Other spectroscopy techniques may work as well.

Another embodiment of the invention provides a method of making a high surface area solid material for collecting at least one analyte, such as a vaporous chemical. The method comprises synthesizing zinc sulfide using a template composition, preparing a solution comprising gold nanoparticles, silver nanoparticles or copper nanoparticles, and depositing the gold, silver or copper nanoparticles onto the zinc sulfide. For example, the step of synthesizing zinc sulfide may include reacting zinc chloride and sodium sulfide in the presence of a template compound. The template compound may optionally be a surfactant, such as an organic surfactant selected from the group consisting of cetyl trimethyl ammonium bromide and alkoxylate block polymers. Preferably, the method further includes calcining the zinc sulfide to thermally decompose the template composition. Furthermore, the zinc sulfide may be acid washed to remove the thermally decomposed template composition.

Gold nanoparticles may be prepared from hydrogen tetrachloroaurate. Deposition of the gold nanoparticles optionally includes mixing the zinc sulfide reaction product with a solution of the gold nanoparticles. The resulting zinc sulfide/gold nanoparticle nanocomposite is preferably washed and dried before use. Solid materials made in accordance with these methods are highly desirable.

Yet another embodiment of the invention provides a solid material made in accordance with the foregoing method. It is most preferred that the zinc sulfide material is substantially optically transparent at wavelengths ranging from 0.45 to 14 micrometers (22,000 to 750 cm$^{-1}$). The solid material may also be characterized by a vapor absorption capacity at least 100 times greater than the absorption capacity of bulk zinc sulfide.

A still further embodiment of the invention provides a spectroscopic detector comprising a nanocomposite of gold, silver or copper nanoparticles deposited on zinc sulfide, and a spectrometer selected from infrared and ultraviolet-visible. The most preferred detectors may be characterized in that the gold, silver or copper nanoparticles provide an enhanced spectroscopic response, and/or characterized by an improved signal to noise ratio. A fan or other fluid flow device may be used to direct a flow of an analyte-containing fluid, such as a vapor-containing gas or air, over the surface of the nanocomposite.

DETAILED DESCRIPTION OF THE PREFERRED EMBODIMENTS

Figure 1:
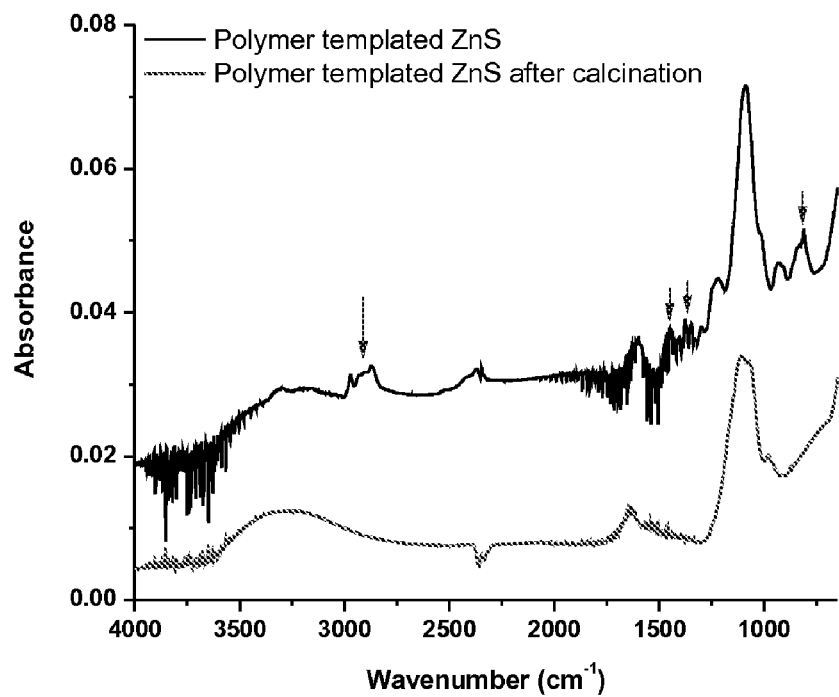
FIG. 1 is a graph of absorbance versus wavenumber for polymer-templated ZnS before and after calcination.

One embodiment of the present invention provides a novel high surface area, high optical quality nanocomposite material with gold nanostructures deposited on the surface. The material of the invention facilitates a combination of solid phase extraction techniques to collect at least one analyte from a very dilute sample, infrared spectroscopy to positively identify a compound by molecular fingerprinting, and the very high sensitivity of surface enhanced Raman spectroscopy, to detect (capture and identify) trace amounts of the at least one analyte, such as a chemical warfare agent and other hazardous organic or inorganic vapors in air. The novel high surface area, high optical quality nanocomposite material of the invention also shows excellent solid phase extraction properties and enables direct spectroscopic interrogation of the at least one collected analyte without requiring any additional processing steps. Furthermore, the nanocomposite material offers enhanced spectroscopic responses, leading to significantly improved signal to noise ratios. The mechanism of analyte collection may include adsorbing, absorbing, and preconcentrating.

The nanocomposite material provides active surfaces with nanometer architectures of metals. Metal nanoparticles can be synthesized in different sizes and shapes, thus, their optical properties can be controlled. This nanocomposite material provides a material that is versatile and generates strong and reproducible spectroscopic signals.

The supporting material should have high or substantial optical transparency in the mid IR range. Examples of suitable optically transparent materials include, but are not limited to, barium fluoride, cadmium telluride, calcium fluoride, cesium iodide, diamond, gallium arsenide, germanium, potassium bromide, potassium chloride, potassium iodide, silicon, silver bromide, silver chloride, silver iodide, sodium chloride, strontium fluoride, zinc selenide, zinc sulfide, and zirconium dioxide. Furthermore, these materials should be prepared in manner that provides a high surface area, such as greater than 100 square meters per gram. Methods for synthesizing high surface area materials suitable for the present invention include, but are not limited to, using a template composition, hydrothermal growth, sol-gel condensation, vapor deposition, and selective etching.

The preferred optically transparent support material is zinc sulfide. Zinc sulfide is substantially optically transparent in a relatively wide wavelength range, 0.45-14 micrometers (22,000-750 cm$^{-1}$). Zinc sulfide that has been synthesized in the presence of surfactants or other template compounds exhibits high surface area that is capable of collecting trace amounts of at least one analyte from a fluid, such as collecting a chemical warfare agent from air, and make them detectable by a spectroscopic method. The optical quality and high loading capacities of the calcined and templated zinc sulfides is a prerequisite for spectroscopic detection of a collected analyte.

The most preferred optically transparent material is a zinc sulfide having a high surface area to increase the adsorption of organic chemicals. The most preferred zinc sulfide is prepared using a surfactant-templated synthetic route, followed by removal of the template. An exemplary reaction is set out in Equation 1, below. In the presence of a template molecule, such as a surfactant, the ZnS formed by the reaction can be given high porosity. For example, the templated material has been shown to be capable of exhibiting a high surface area in excess of 100 square meters per gram (m$^2$/g). A surface area density of between 100 and 300 square meters per gram is suitable, but the surface area density is preferably as high as economically achievable. It is believed that the high surface area is due, in large part, to the small particle size, but may also be attributable to porosity of the particles, such as mesoporosity.

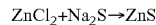

$$ZnCl_2 + Na_2S \rightarrow ZnS \qquad \text{Equation (1)}$$

The pH has been found to affect the purity of the ZnS. Specifically, a low pH between about 2 and about 5 is desirable. Higher pH during the reaction leads to greater formation of ZnO that will produce its own spectroscopic signal. Still, depending on the analyte(s) of interest, the presence of small amounts of ZnO may not be detrimental.

The preferred templates are generally referred to as surfactants. A preferred surfactant is a polyoxyalkylate, such as a block copolymer of ethylene oxide and propylene oxide. A specifically preferred polyoxyalkylate is a EO$_{20}$/PO$_{70}$/EO$_{20}$ triblock copolymer. However, there are many alternative polyoxyalkylates or other surfactants that may also work well as templates. A suitable template should produce a high surface area material and be easily removed from the material, such as by calcination and/or washing. For this purpose the template is preferably organic, but may also be inorganic.

The template compound may be removed from the composite material through calcination. The composite is preferably calcined or heated in air to a temperature of about 400°

C. in order to burn off the organic template. Typically, the optically transparent material will be washed with water after the calcination.

Nanoparticles of a selected metal may be deposited on the surface of the material to provide signal enhancement during spectroscopic analysis. Typically, the metal nanoparticles will be selected from silver, gold, copper, platinum, palladium, iron, rhodium, and alloys thereof. The preferred metal nanoparticles are gold and silver nanoparticles. Gold nanoparticles are the most preferred, especially triangular gold nanoparticles because they have been found to provide a ten-fold spectroscopic signal enhancement when used in accordance with the present invention.

The very high surface area of templated zinc sulfide materials, and presence of sulfur on the surface has also been found to provide an excellent material for attachment of gold, silver or copper nanoparticles. Both the gold and silver nanoparticles have been found to adhere well to the zinc sulfide surface. In addition, zinc sulfide is also hard, compatible with most chemicals, readily available and inexpensive. The nanoparticles are preferably placed on the ZnS material using solution phase colloidal gold deposition. Advantageously, it has been determined that the triangular gold nanoparticles, which produce a blue colored solution, preserve their shape after deposition on the ZnS.

The invention combines the preparation of uniform metal nanostructures in colloidal form and the preparation of optically transparent materials with extremely high surface area to provide a new composite material that has nanostructured metals deposited onto the optically transparent material featuring high surface area. This composite material is shown to be ideal for both preconcentration of an analyte on the solid phase extraction material and spectral detection using surface-enhanced infrared (SEIR) and/or surface-enhanced Raman scattering (SERS). The optical quality of the templated zinc sulfides is improved by calcinations to remove residual organic materials.

The spectroscopic detection preferably uses infrared spectra or ultraviolet-visible spectra, specifically including, without limitation, diffuse reflectance infrared Fourier transform (DRIFT) spectroscopy and attenuated total reflection (ATR) infrared spectroscopy. Other spectroscopic methods that are compatible with the nanocomposites of the invention will be recognized by those in the art having the benefit of the present disclosure and these other spectroscopic methods are considered within the scope of the present invention.

Surrogates of all three major classes of chemical warfare agents can be pre-concentrated and spectroscopically detected, even in the presence of interfering contaminants, using the novel nanocomposite materials of the present invention. These results clearly demonstrate the utility and surprising results of the nanocomposite material, a spectroscopic detector and an air sampling system. Using the present invention, various organic chemicals can be collected and identified by their distinguishable infrared spectroscopic signals.

Figure 11:
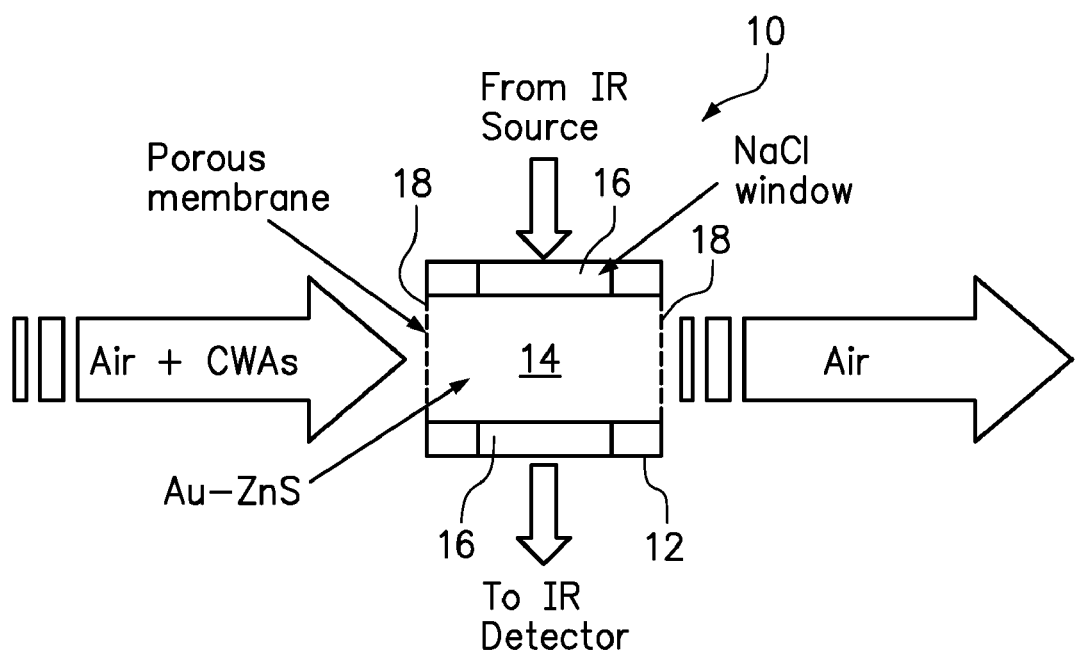
FIG. 11 is a schematic diagram of an air sampling device utilizing the composite materials for direct detection of organic chemical vapors.

FIG. 11 is a schematic diagram of an air sampling device 10 utilizing the composite materials for direct detection of organic chemical vapors. In one embodiment, a ZnS—Au composite, for example, is incorporated into a sample cartridge 12 that may be disposable. The cartridge may be equipped with a chamber 14 to contain the composite material during collection and spectroscopic detection of a known or unknown analyte or analyte mixture. Such a cartridge may also be provided with opposing infrared transparent windows 16 made of inexpensive NaCl or KBr to allow an infrared beam to pass through a first window into the chamber 14, through the composite material, and out of the cartridge through an opposing window. In this manner, the only material in the path of the IR beam that is not IR transparent is the analyte that collects onto the composite material. The optical path length through the composite material is presently thought to be most appropriate between 0.5 mm and 5 mm, although particular arrangements and equipment should be optimized to obtain a high signal to noise ratio.

The cartridge 12 also includes a fluid passageway, such as an air passageway, through the chamber 14 so that an analyte in the fluid, such as an organic chemical vapor in the air, comes into direct contact with the composite. In one embodiment, the fluid (a gas or liquid) passes through opposing porous membranes or filters 18 that retain the composite material within the chamber 14, but allow the entry and exit of the fluid. Most conveniently, the fluid pathway and the IR beam pathway may be disposed at an angle, such as nearly perpendicular, to avoid obstructing either pathway's access to a small amount of composite material. The porous membrane 18 does not have to be IR transparent since it is not disposed in the path of the IR beam. The porous membrane should have sufficient porosity to allow fluid passing through with minimal resistance, be rugged, and avoid collecting any of the targeted analyte chemicals. One suitable porous membrane is made from polytetrafluoroethylene. In one embodiment, a fan may be used to push or pull an analyte-containing gas, such as an analyte vapor-containing air, through the chamber and into intimate contact with the composite material. Furthermore, a non-adsorbent filter may be positioned to remove particulates from the gas or air prior to making contact with the composite. Most preferably, the entire system may be made portable.

In accordance with the present invention, the results of the spectroscopic detection may be qualitative, quantitative, or both. The IR spectroscopy is primarily quantitative in that it identifies organic chemicals that collect on the surface of the composite material. However, it may also be possible to calibrate the instrumentation to provide a quantitative result.

In another embodiment, a high surface area, optically transparent material, such as a templated zinc sulfide, is admixed with a polymeric binder to enable formation of substantially optically transparent pre-concentrator films and membranes. Preferred polymeric binder materials include, but are not limited to, fluorinated organic polymers. A particularly preferred polymeric binder is polytetrafluoroethylene. The powdered zinc sulfide material, for example, can be dispersed in a solution or suspension of the binder polymer in an organic or aqueous solvent. The resulting mixture can be used to cast films or membranes using drop or spin-casting, and other techniques known to those skilled in the art. After evaporating the solvent or mixture of solvents, the film can optionally be cured at elevated temperatures to achieve a stronger bond between the zinc sulfide and the polymeric binder.

In a still further embodiment, an optically transparent material, such as zinc sulfide, is directly deposited onto a solid substrate to form a coating. The solid substrate preferably has a gold surface, because the affinity between sulfur and gold forms a secure coating; gold is also reflective to infrared light, and is otherwise chemically inert. However, the solid substrate may be made from many other materials, such as plastic, glass, ceramic and metals. A particularly preferred solid substrate is a gold on titanium on glass substrate. These large solid substrates can form plates, beads, or other shapes suitable for analyte collection and handling.

The coatings may be formed by applying an aqueous slurry of an optically transparent material over a clean gold substrate surface, then drying the slurry. The optically transparent materials are preferably selected from the group consisting of KBr, AgCl, ZnSe, NaCl, CsF or ZnS, where ZnS is the most preferably optically transparent material. The coating will preferably include from 1 nanogram/cm$^2$ to 10 mg/cm$^2$ of the optically transparent material and most preferably between 1 mg/cm$^2$ and 3 mg/cm$^2$. When the coating is dry, the coated substrate is ready for use. Other substrates are also possible, but should be either spectroscopically transparent or reflective. Non-limiting examples of spectroscopically transparent substrates include crystalline ZnS and ZnSe, whereas non-limiting examples of reflective substrates include metals such as Pt, Pd, Al, Ag, and Zn. Optionally, gold nanoparticles may be deposited onto the surface of the coating material in order to enhance the spectroscopic signal. In a further option, a binder could be included in the coating.

EXAMPLES

In the following examples, the chemicals were obtained from Aldrich, Fluka and Strem, and were used as received. Infrared spectra were recorded on a FTIR spectrophotometer equipped with a single reflection ATR accessory. Ultraviolet-visible (UV-VIS) spectra were recorded using a double beam UV-VIS spectrophotometer. GC-MS experiments were performed on a gas chromatograph equipped with a mass spectrometric detector. Samples were exposed to agent surrogates in a vacuum desiccator at atmospheric or reduced pressure.

Example 1

Synthesis of ZnS Using Cetyl Trimethyl Ammonium Bromide (CTAB) as Template

Materials templated with cetyl trimethyl ammonium bromide (CTAB) were synthesized by dissolving 3.0 g of zinc chloride and 1.9 g of CTAB in 50 mL water and subsequent addition of 6.0 g of sodium sulfide dissolved in 50 mL water with continuous stirring. The pH of the mixture was then adjusted to 6 by adding 6 M hydrochloric acid, and the mixture was allowed to stand in the fume hood for 4 days, washed with water, refluxed in ethanol for 2 days and dried in a vacuum oven. The yield was determined to be 1.24 g of the CTAB-templated material.

Example 2

Synthesis of ZnS Using a Pluronic Copolymer as the Template

In a manner similar to Example 1, other polymer-templated materials were synthesized by first dissolving 3.0 g of zinc chloride and 3.0 g of PLURONIC 123 copolymer (PLURONIC 123 is a trademark of BASF Corporation in New Jersey, identified as an $EO_{20}/PO_{70}/EO_{20}$ triblock copolymer) in 50 mL of water. To this solution were added 6.0 g of sodium sulfide dissolved in 50 mL of water under continuous stirring. The pH was adjusted to 6 by adding 6 M hydrochloric acid, and the resulting mixture was allowed to stand in fume hood for 4 days. The crude product was rinsed with water and ethanol, as described above, and dried in a vacuum oven. The yield was determined to be 1.6 g of the copolymer-templated material.

Example 3

Template Removal

The material samples obtained in Examples 1 and 2 were each placed in a ceramic crucible and calcined in a muffle furnace at 400° C. in air for 1-3 days. The calcined materials were then suspended in 0.01 M hydrochloric acid and agitated for 15-20 minutes. The solids were collected by centrifugation, washed with deionized water and methanol, and finally dried in a vacuum.

Calcination at moderately high (400-600° C.) temperatures was used to quantitatively remove organic matter, because the absence of organic residues is expected to improve both the optical transparency in the mid-IR range and the amount of gold nanoparticles that can be adsorbed onto the surface. However, since metal sulfides are susceptible to oxidation, the calcination temperature was carefully adjusted to about 400° C. This temperature was sufficient to completely eliminate organic residues while preventing the zinc sulfide from being oxidized. Calcination and characterization were performed as described below.

The infrared spectra are presented in FIG. 1 and show that calcination completely removed residual organics. Bands at 3000-2800, 1460, 1375 and 815 cm$^{-1}$ in the upper spectrum of the as-synthesized ZnS due to the residual template materials are absent in the calcined sample, clearly demonstrating superior optical transparency in the mid-IR.

Figure 2:
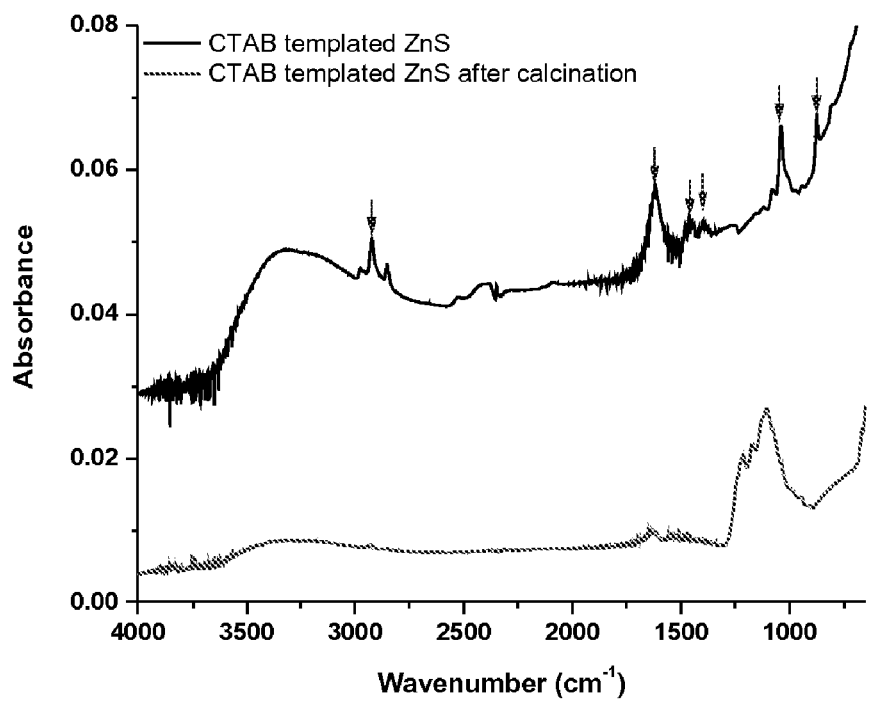
FIG. 2 is a graph of absorbance versus wavenumber for cetyl trimethyl ammonium bromide-templated ZnS before and after calcinations.

Similarly, porous zinc sulfide materials that were prepared using CTAB as the template material were calcined at 400° C. FIG. 2 shows that the absorbance bands present at around 3000-2800, 1620, 1460, 1400, 1050 and 880 cm$^{-1}$ in the spectrum of the as-synthesized material are completely absent in the calcined sample, again demonstrating high optical transparency. However, absorbance in the 1200-1000 cm$^{-1}$ region indicated the presence of trace oxidation products.

As discussed above, the optical transparency of the high surface area ZnS materials could be significantly improved by calcining at 400° C. However, as evidenced by infrared spectroscopy, some oxide species were present in the calcined samples. Since both zinc oxide and oxidized sulfur species (sulfite, sulfate, etc.) are soluble in slightly acidic water, these contaminants can be easily removed by washing with dilute hydrochloric acid.

Figure 3:
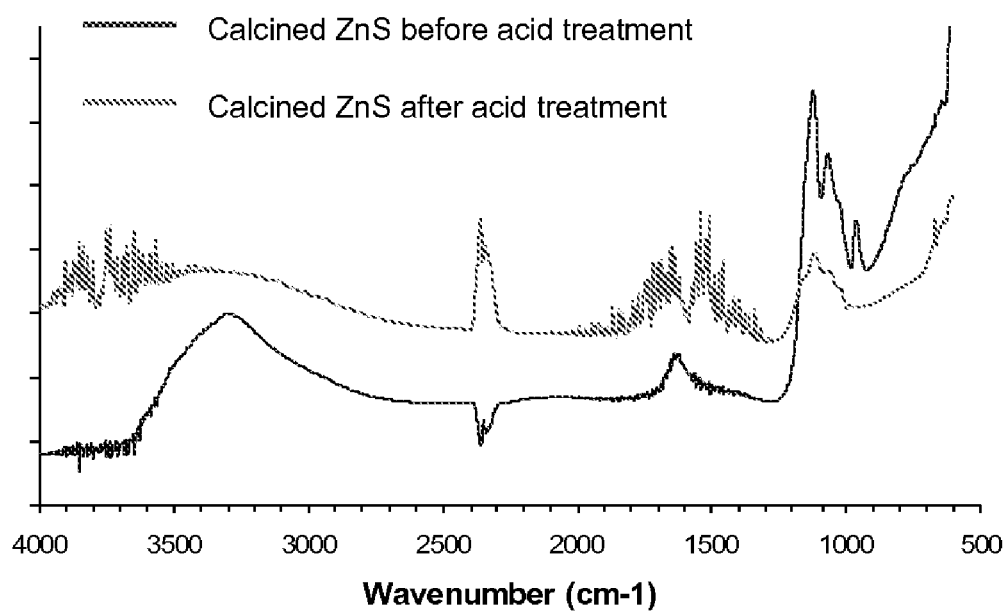
FIG. 3 is a graph of absorbance versus wavenumber for calcined ZnS before and after acid treatment.

FIG. 3 shows infrared spectra of calcined CTAB-templated materials before and after acid treatment. While the untreated sample exhibits relatively prominent absorptions at 1600 cm$^{-1}$ and 1200-900 cm$^{-1}$, assigned to ZnO and sulfur-oxygen species, respectively, these signals are substantially decreased in the acid-treated sample, offering even better optical and spectral transparency.

Example 4

Synthesis of Branched Gold Nanoparticles and Deposition onto Support Materials

Branched gold nanocrystals were synthesized by adding 8 mg of bis-(p-sulfonatophenyl) phenyl-phosphine dihydrate dipotassium (BSPP) and 0.2 mL of 30% hydrogen peroxide into 100 mL of 6.8 mM sodium citrate solution, and filtered. 0.2 mL of 0.05 M hydrogen tetrachloroaurate was added with stirring. A blue coloration developed within one minute indicating formation of branched and triangular nanostructures of gold. The resulting colloidal solution was then immediately deposited onto the ZnS without any workup or purification.

Example 5

Deposition of Gold Nanoparticles onto ZnS Pre-Concentrator Material to Enhance Spectroscopic Signals 100 mg of the calcined and washed porous ZnS material obtained from Example 3 was added to a freshly prepared solution of branched gold nanoparticles according to Example 4 with vigorous stirring. After 4-5 hours, the solids were collected by centrifugation, washed with DI water and methanol, and dried. Residual organic matter (such as citrate) was removed by calcinations at 350-400° C. for 12 hours, followed by washing with 0.01 M HCl, deionized water and methanol. The bluish-purple powders were finally dried in a vacuum. Brunauer Emmett Teller (BET) measurements were carried out on the high surface area zinc sulfide-gold nanocomposite materials to determine that the overall surface area was 105 $m^2/g$.

Gold nanoparticles are attached onto the ZnS substrates by immersing the high surface area ZnS materials (100 mg/100 ml of Au colloidal solution) in a freshly prepared solution of branched gold nanoparticles. Over the course of 1-2 hours, the ZnS powder obtained bluish-purple coloration, indicating a successful deposition. The mixture remained blue even after three days at room temperature indicating the fixation of the branched gold nanoparticles onto zinc sulfide.

Figure 4:
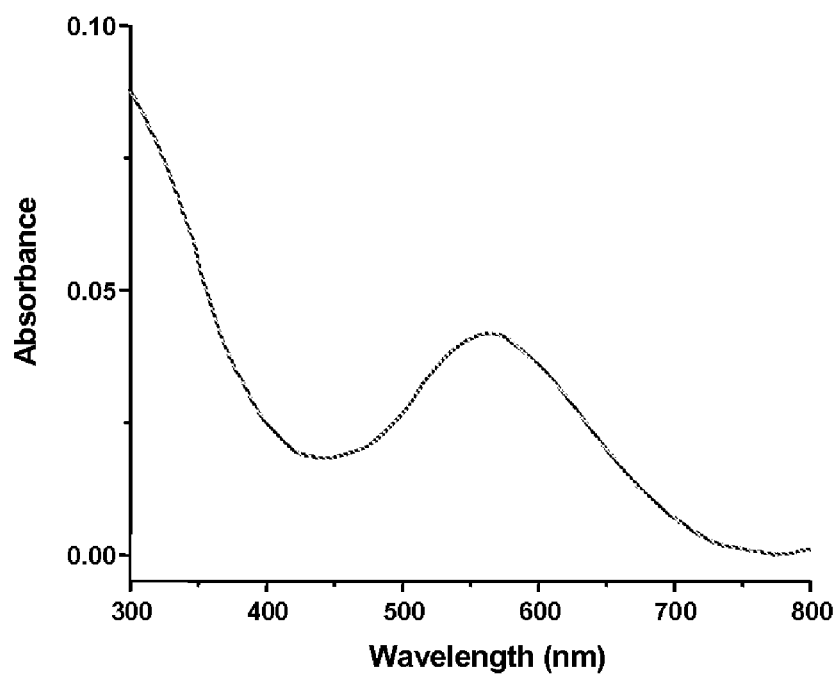
FIG. 4 is a graph of absorbance versus wavelength for a composite having gold nanoparticles deposited on templated ZnS.

Since the shape and absolute position of the surface plasmon resonance band of metal nanoparticles is highly sensitive to size and morphology changes, reflectance UV-vis spectroscopic investigations of the composite materials were performed. A representative spectrum is shown in FIG. 4, which features a relatively sharp and symmetrical band centered at 580 nm, strongly indicating that the overall morphology of the gold nanoparticles is preserved during the deposition process.

Example 6

Figure 5:
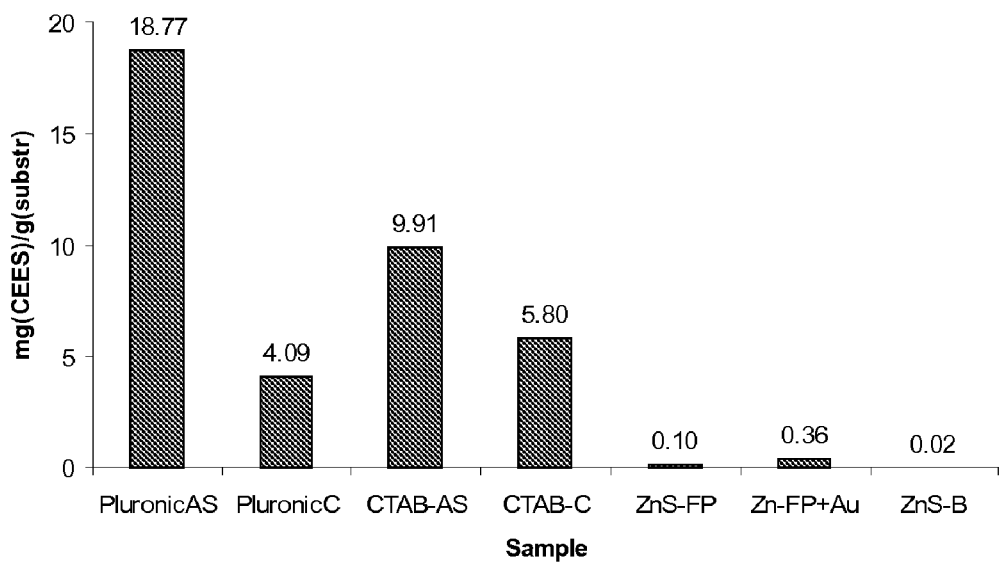
FIG. 5 is a bar chart of the CEES loading capacity of various forms of ZnS.

Assessment of Solid Phase Extraction Capacity Using Chemical Agent Surrogate Adsorption In addition to the optical properties discussed above, the solid phase extraction capabilities of the newly synthesized materials were also investigated. To determine the maximum adsorption capacity for CWA surrogates, the material samples prepared in Examples 1, 2, 3, 4 and 5 were exposed to saturated vapors of 2-chloroethyl ethylsulfide (CEES) at ambient temperature for 16 hours. The samples were extracted with dichloromethane and analyzed by GC/MS to determine the amount of surface-bound agent surrogate. The new materials showed much higher loading capacities compared to commercially available bulk ZnS materials. We observed adsorption capacities to be up to 900 times higher for as-synthesized (PLURONIC-AS and CTAB-AS in FIG. 5) and up to 300 times higher for template removed (PLURONIC-C and CTAB-C) high surface area zinc sulfides compared to that of the bulk zinc sulfide. In relation to FIG. 5, AS stands for "as synthesized", C stands for "calcined", B stands for bulk, and FP stands for "fine powder of bulk".

Example 7

Detection of Agent Surrogates Using Reflectance Infrared Fourier Transform Spectroscopy In order to demonstrate spectroscopic detection of CWA surrogates, samples of the optimized ZnS/Au materials were exposed to vapors of 2-chloroethyl ethylsulfide (CEES), diethyl methylphosphonate (DEMP), and tributylphosphate (TBP), respectively. CEES, for example, was then detected and identified by Reflectance Infrared Fourier Transform spectroscopy on the high surface area ZnS/Au substrate materials. Spectra of the exposed ZnS/Au materials exhibited absorption bands at 2950, 1450, 1150, 800 and 700 $cm^{-1}$, characteristic for CEES. In contrast, these bands were not observed on unexposed control ZnS/Au materials.

Example 8

Figure 6:
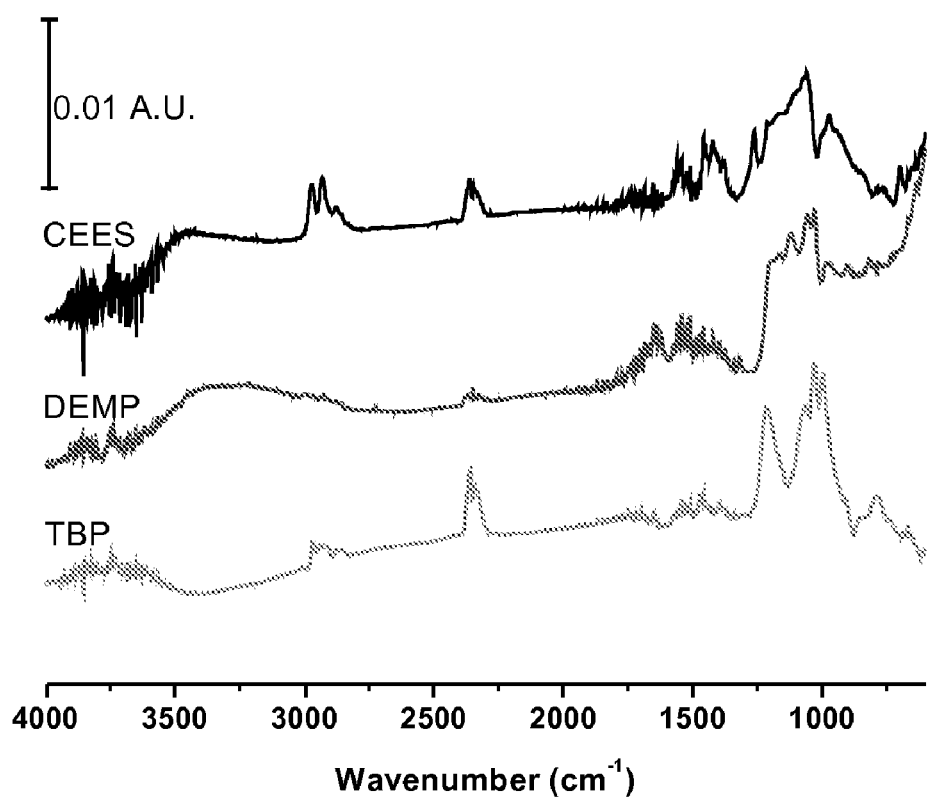
FIG. 6 is a graph of absorbance versus wavenumber for the ATR infrared spectroscopy of CEES, DEMP and TBP collected on ZnS solids.

Detection of Agent Surrogates Using Attenuated Total Reflection (ATR) Infrared Spectroscopy Experiments similar to those of Example 7 were carried out using a basic single reflection attenuated total reflection (ATR) instrumental setup. Samples of the ZnS/Au nanocomposite were exposed to vapors of all three surrogates, CEES, DEMP and TBP, and probed the spectroscopic responses. The results are shown in FIG. 6. Strikingly, all three surrogates can be detected and identified using a very basic instrumental setup and characteristic absorptions were observed on the exposed samples, whereas no signals were detected on the control.

Figure 7:
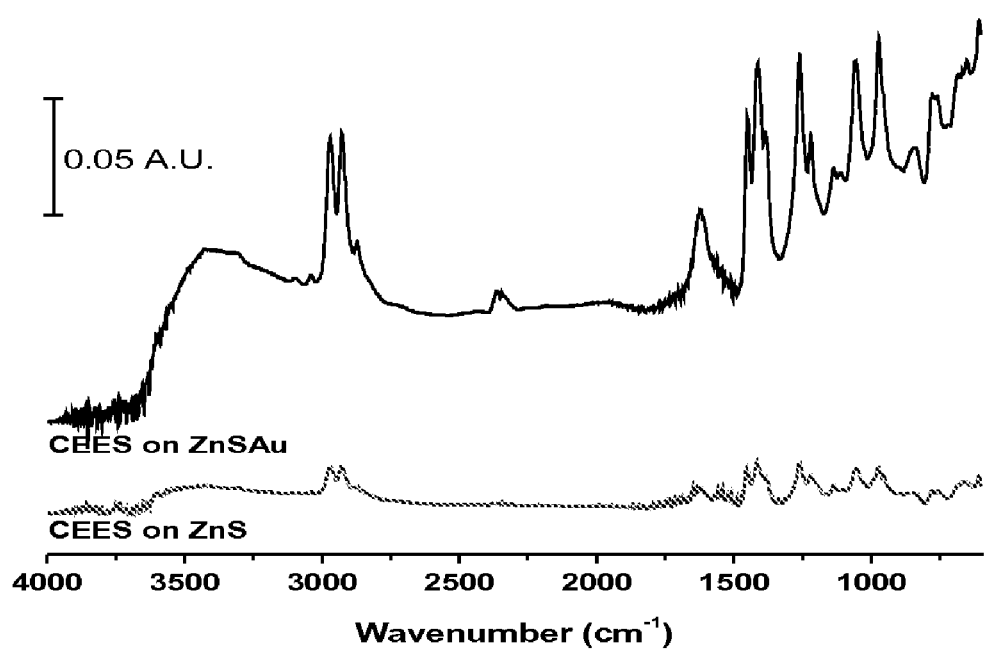
FIG. 7 is a graph of absorbance versus wavenumber for CEES on templated ZnS solids with and without gold nanoparticles deposited on the ZnS surface.

Furthermore, the effects of gold nanoparticles on the spectroscopic response were examined by exposing ZnS samples with and without deposited gold particles to CEES. FIG. 7 shows representative spectra of CEES collected on both materials. As can be seen, the signals arising from the gold-containing ZnS samples are more than four times as strong as compared to the bare ZnS substrate, indicating a significant enhancement of the spectroscopic response. It was then determined that concentrations as low as 100 ppb of CEES in air were detectable using the ZnS/Au nanocomposites. These results clearly demonstrate that substantially optically transparent, high surface area ZnS/Au composites are well-suited to pre-concentrate airborne analytes and simultaneously allow spectroscopic detection and identification of CWAs.

Example 9

Detection of Agent Surrogates in the Presence of Interfering Fuel Vapors

Figure 8:
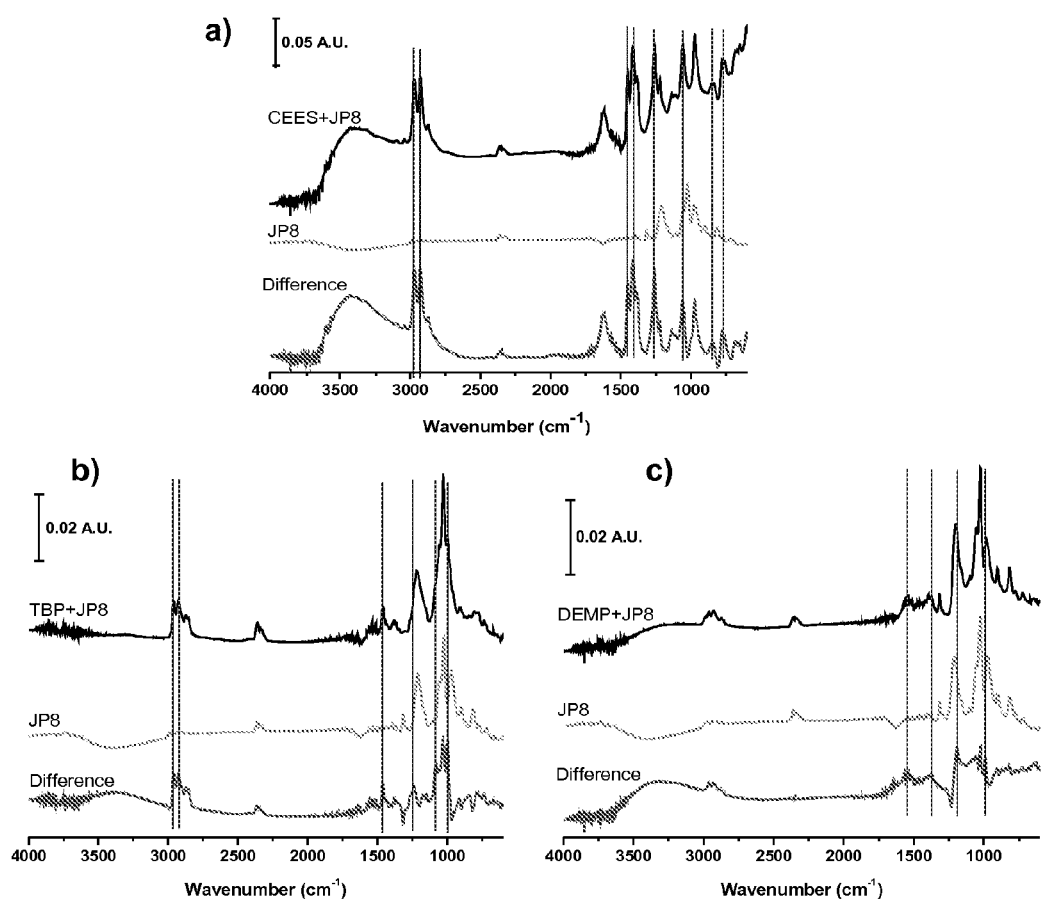
FIGS. 8A-C are graphs of absorbance versus wavenumber for each of three agent surrogates in a mixture with JP-8 fuel.

Detection of one or more specific analyte in the presence of one or more interfering species presents a major challenge for existing, less specific detection technologies. The ability to detect at least one specific analyte against a complex background of fluids therefore provides a significant improvement over existing technologies. Samples of ZnS/Au composites were exposed to mixed vapors of agent surrogates and JP-8 fuel. The spectroscopic responses of the exposed ZnS/Au composites were then probed in accordance with the ATR infrared spectroscopy as described in Example 8. FIGS. 8A-C show that the characteristic spectroscopic fingerprints for each of the three surrogates can be extracted from a complex mixed spectrum, which in turn enables unambiguous identification of hazardous chemicals and will significantly reduce, if not prevent, false positive detector responses.

Example 10

Detection of Agent Surrogates in the Presence of Water Vapors

CEES was detected even in the presence of high relative humidity (RH). Zinc sulfide substrates with gold nanoparticles, in accordance with Example 5, were exposed to CEES vapor at 0% RH and at almost 100% RH. The IR absorption bands for CEES at 100% RH were clearly distinguishable and fully comparable to those at 0% RH. However, broad absorption bands in the 3400 cm$^{-1}$ and 1600 cm$^{-1}$ regions due to the collection of water vapor were observed in the samples exposed to high RH.

Example 11

Effect of Reactant Ratios on Particle Surface Area

The surface area of zinc sulfide particles is a function of their size and porosity. It was believed that the surface area of the zinc sulfide particles would depend upon the surfactant concentration and morphology, as well as the effective concentration of the precursor ions ($Zn^{2+}$ and $S^{2-}$). Accordingly, an array of different materials was prepared using varying surfactants at varying concentration and varying pH. The pH was varied as a means to control the concentration of free precursor ions (high pH decreases $Zn^{2+}$ concentration and low pH decreases $S^{2-}$ concentration).

An array of 18 different materials was prepared and their adsorption capacities were determined using GC-MS. The synthesis was carried out using aqueous solutions of zinc chloride and sodium sulfide. The following concentrations were employed: $c(Zn^{2+})$=220 mM and $c(S^{2-})$=250 mM were kept constant throughout; surfactant type and concentrations were c(Pluronic)=15; 30; 60 g L$^{-1}$, denoted as P-1, P-2, and P-3, respectively, and c(CTAB)=8; 16; 32 g L$^{-1}$, denoted as C-1 through C-3. To adjust the pH, hydrochloric acid was added to c(HCl)=200; 150; 100 mM, denoted as H-1, H-2, and H-3. The materials formulations are summarized in Table 1 below.

TABLE 1

Reactant ratios and materials synthesized.

| Entry | Surfactant* | Surfactant concentration (g/L) | HCl conc. (mM) |
|---|---|---|---|
| P-1/H-1 | Pluronic 123 | 15.00 | 200 |
| P-1/H-2 | Pluronic 123 | 15.00 | 150 |
| P-1/H-3 | Pluronic 123 | 15.00 | 100 |
| P-2/H-1 | Pluronic 123 | 30.00 | 200 |
| P-2/H-2 | Pluronic 123 | 30.00 | 150 |
| P-2/H-3 | Pluronic 123 | 30.00 | 100 |
| P-3/H-1 | Pluronic 123 | 60.00 | 200 |
| P-3/H-2 | Pluronic 123 | 60.00 | 150 |
| P-3/H-3 | Pluronic 123 | 60.00 | 100 |
| C-1/H-1 | CTAB | 8.00 | 200 |
| C-1/H-2 | CTAB | 8.00 | 150 |
| C-1/H-3 | CTAB | 8.00 | 100 |
| C-2/H-1 | CTAB | 16.00 | 200 |
| C-2/H-2 | CTAB | 16.00 | 150 |
| C-2/H-3 | CTAB | 16.00 | 100 |
| C-3/H-1 | CTAB | 32.00 | 200 |
| C-3/H-2 | CTAB | 32.00 | 150 |
| C-3/H-3 | CTAB | 32.00 | 100 |

*CTAB: cetyl trimethylammonium bromide; Pluronic 123: poly(ethylene oxide-b-propylene oxide-b-ethylene oxide), MW = 5,800.

In order to determine adsorption capacities, the materials were exposed to saturated vapors of 2-chloroethyl ethyl sulfide (CEES) in air at ambient temperature for 12 hours. The materials were extracted with dichloromethane, and the amount of surface-bound CEES was determined using GC-MS. The results are summarized in FIG. 9A.

Figure 9A:
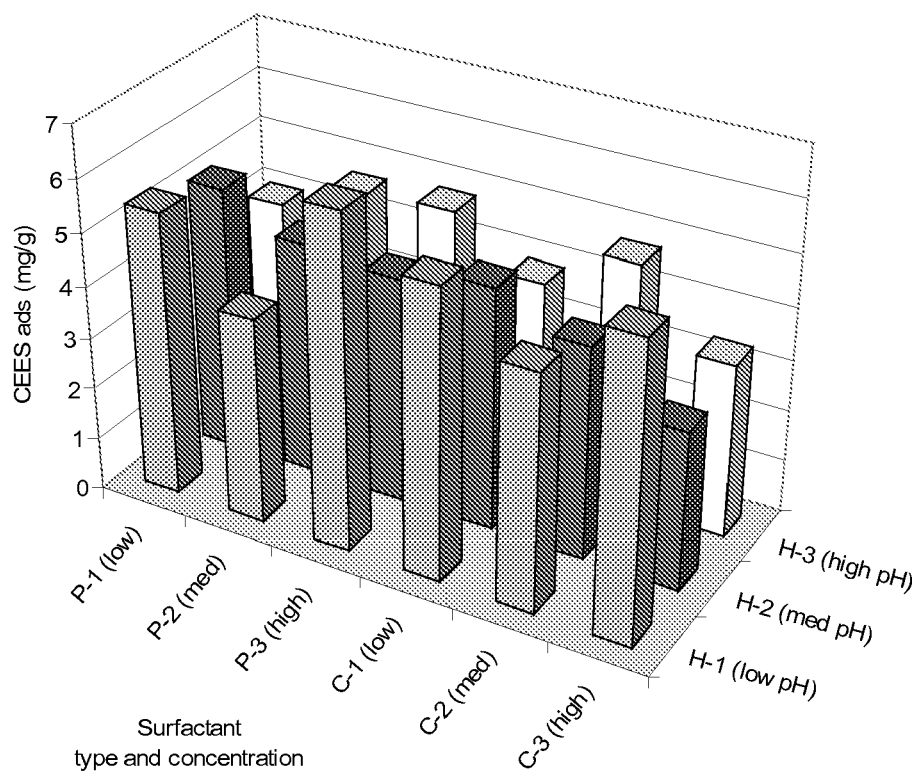
FIGS. 9A-C are bar graphs of CEES, DEMP, and TBP adsorption capacities as a function of surfactant template type, surfactant template concentration, and pH during formation of different materials.

While all material compositions showed significant uptake of CEES (>3 mg/g), it can be seen from FIG. 9A that lower pH generally produced materials with higher adsorption capacity. Furthermore, the Pluronic template favored higher capacity materials (up to 6.4 mg/g for P-3/H-1). However, no clear relation between surfactant concentration and adsorption capacity was established.

The adsorption capacities were determined by exposing the materials to saturated vapors of DEMP and TBP in air at ambient temperature for 12 hours. The materials were extracted with dichloromethane, and the amount of surface-bound agent surrogate was determined using GC-MS. The results are summarized in FIGS. 9B and 9C.

Figure 9B:
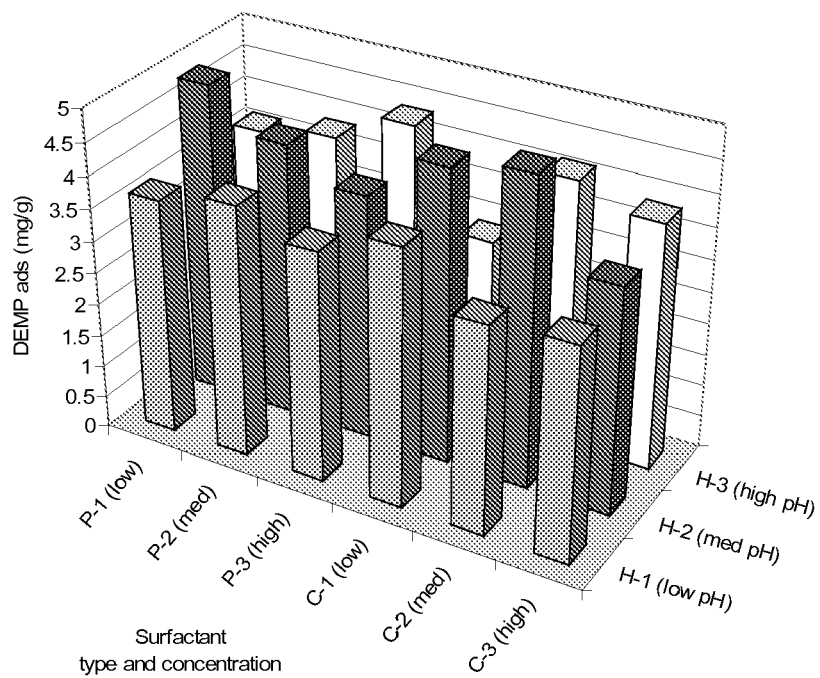
Figure 9C:
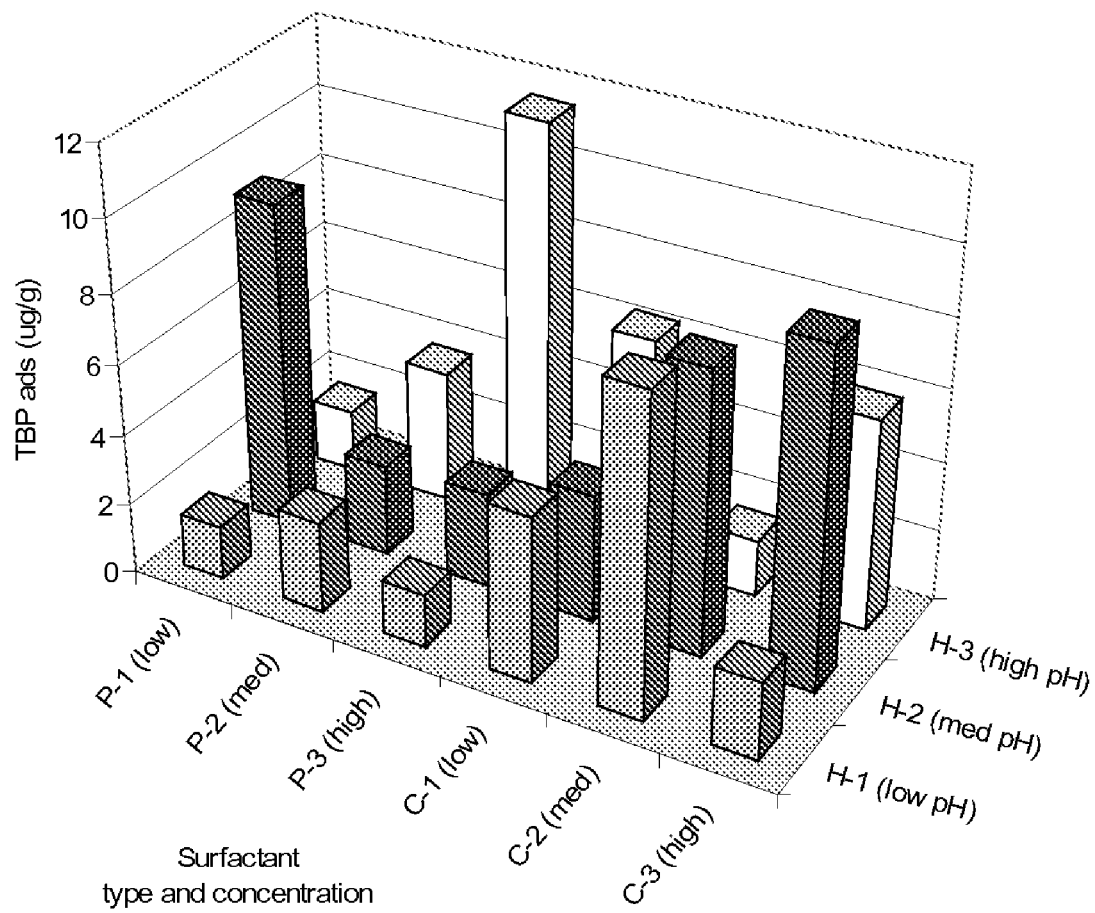

All material compositions showed significant uptake of DEMP (>3 mg/g). As indicated in FIG. 9B, the materials synthesized at intermediate pH show the highest uptake. However, no clear relation between surfactant concentration and adsorption capacity could be established. As seen in FIG. 9C, the uptake of TBP was considerably lower (<12 μg/g), due to the extremely low vapor pressure of TBP. The low overall uptake may also explain the apparent variation in uptake; the TBP concentrations are only slightly above the detection limit of the GC-MS instrument used, which might account for significant instrumental error.

Based on the uptake of CEES and DEMP, nine material formulations were selected for further characterization using FTIR. Infrared spectra were recorded for the blank materials, as well as for the materials exposed to CEES, DEMP, and TBP, respectively.

CEES and DEMP can be readily detected by FTIR on all formulations. Conversely, TBP could only be detected on some materials. Again, this is due to the extremely low vapor pressure of TBP; only very small amounts are collected onto the materials. In addition, while all formulations synthesized at medium and high pH exhibit absorptions bands arising from residual zinc oxide, no oxide absorption could be detected on the materials synthesized at low pH. This result indicates that a higher acid concentration during the synthesis generally suppresses oxide formation and produces higher quality materials.

Example 12

Effect of pH on Optical Purity

Figure 10A:
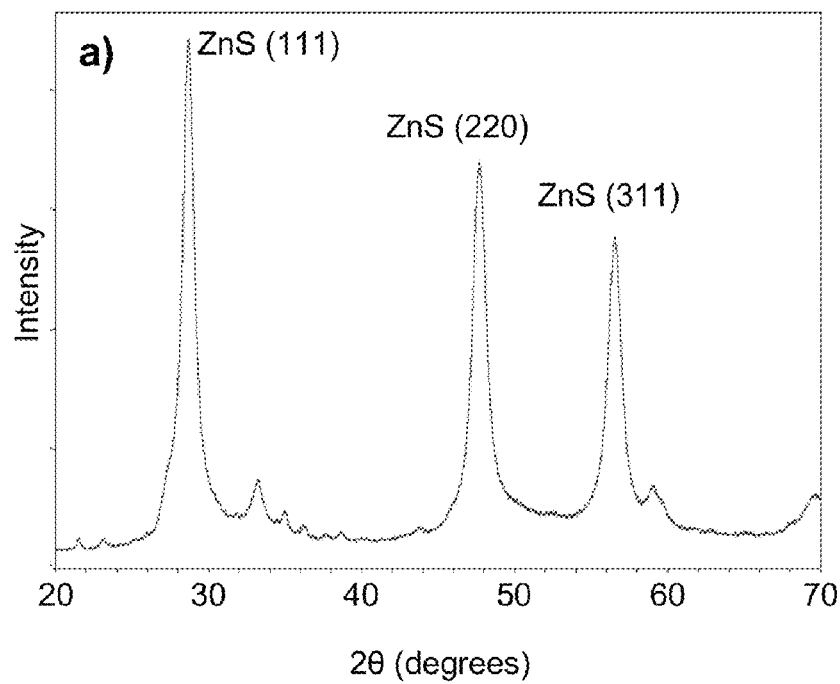
FIGS. 10A-B are graphs of XRD patterns for two different ZnS materials synthesized at low pH (A) and high pH (B).
Figure 10B:
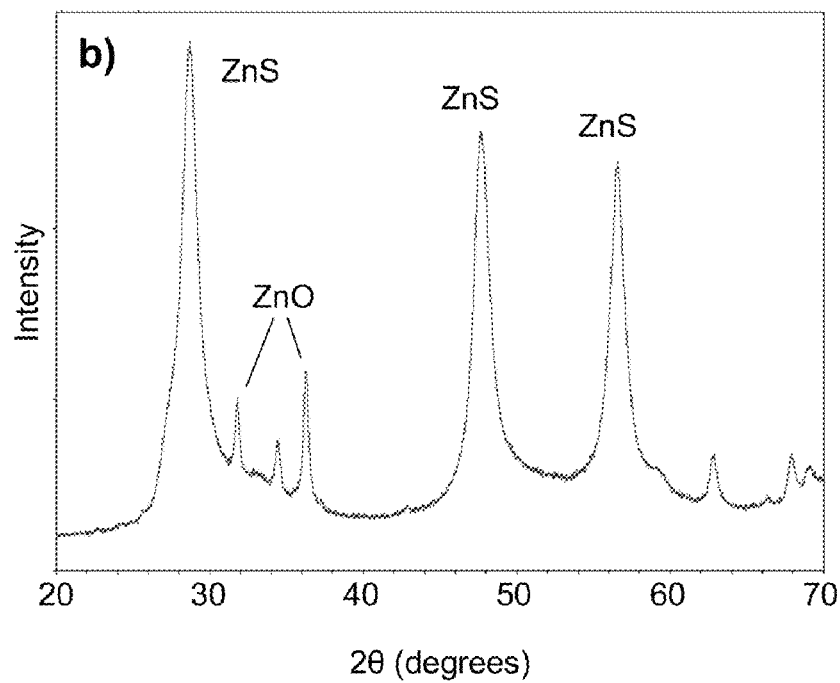

In order to confirm the observation that the ZnS materials synthesized at lower pH generally exhibit lower oxide content and thus improved IR transparency, X-ray diffraction (XRD) experiments were conducted for all 18 material formulations. The diffraction patterns showed that all 18 material formulations consist primarily of cubic zinc sulfide, as evidenced by prominent reflections at 2θ=28.559° (d=3.1230 Å; (111)); 33.090° (d=2.7050 Å; (200)); 47.516° (d=1.9120 Å; (220)) and 56.290° (d=1.6330 Å; (311)). In addition, the samples contained varying amounts of zinc oxide (2θ=31.840° (d=2.8083 Å; (100)); 36.337° (d=2.4704 Å; (101)); 47.653° (d=1.9068 Å; (102)), along with trace amounts of hexagonal zinc sulfide. Two representative patterns are shown in FIGS. 10A and 10B below. FIG. 10A depicts the pattern of formulation P-1/H-1, Pluronic templated at low pH. As can be seen, the sample largely consists of cubic ZnS with only very minor traces of ZnO. In contrast, FIG. 10B depicts the pattern of formulation C-1/H-3, CTAB templated at high pH contains significant amounts of ZnO. These results clearly confirm that low pH generally produces higher quality materials. Furthermore, we observed that the Pluronic-templated materials generally exhibit a higher purity than the CTAB templated formulations.

Example 13

Formation of Zinc Sulfide Films Using a Polymeric Binder

The calcined ZnS materials (1.0 g) obtained in Example 3 were suspended in 2 mL of deionized water. To this suspension were added 0.7 g of a surfactant-stabilized 65 wt % dispersion of polytetrafluoroethylene in water (DuPont). After vigorous stirring, the mixture was used to cast a thin film onto gold coated glass slides. The solvent was left to evaporate under ambient conditions, and the dried supported film was cured at 350° C. in air for 8 hours.

Example 14

Preparation of Zinc Sulfide Coated Gold Substrate

ZnS coated gold on titanium on glass substrates (about ½"×½") were prepared first by cleaning the substrate (gold on titanium on glass) with freshly prepared Piranha solution (1:3, 30% hydrogen peroxide:concentrated sulfuric acid), rinsed with de-ionized water followed by deposition of 10-50 µL of various slurries with different concentrations of ZnS. The ZnS coated substrates were first allowed to dry overnight at room temperature. The substrates were then heated to 200° C. in an oven to remove water completely. The substrates were then characterized visually, by SEM and by FTIR using a single reflectance accessory (30 Spec, Pike Technologies, Madison, Wis.) and a bare gold on titanium on glass substrate as the reference. The materials' morphologies were characterized by SEM. The SEM showed that the ZnS coated gold on titanium on glass substrates had micrometer scale roughness with submicron features (holes) for both 50 µL of 2% ZnS and 20 µL of 10% ZnS.

Example 15

Effect of Zinc Sulfide Coating Thickness on the Capture and Detection of Vapors In Addition, we have also prepared gold substrates coated with various thicknesses (in the range of 1 mg/cm$^2$ to 3 mg/cm$^2$) of ZnS using same volume-different concentrations and same volume-different concentrations of aqueous suspensions of ZnS. The ZnS coated substrates after drying in oven at 200° C. were tested with dimethyl methylphosphonate (DMMP) in nitrogen using the same setup as before. The ZnS coated substrates were exposed to a 2 L/min air flow containing 50 ppt of DMMP for various periods of time and spectra collected.

Fifty parts per trillion (50 ppt) of DMMP in nitrogen at 2 L/min was generated by mixing 4.37 mL/min of saturated DMMP vapor at −10.0° C. with 1.996 L/min of ultra high purity nitrogen using digital mass flow controllers based on the saturated vapor pressure data (1.74×10$^{-5}$ torr at −10° C.).

IR spectra of DMMP captured on the ZnS substrate was collected as before. The substrate was placed on a 30 Spec reflectance accessory in a Bruker Tensor 27 FTIR spectrometer and baseline spectrum recorded (128 scans). The ZnS coated substrate was then placed in the Lynntech's air-sampler/substrate holder and the nitrogen stream containing 50 ppt of DMMP was passed through for various periods of time, placed back in the spectrometer and the sample spectrum recorded (128 scans).

Figure 12:
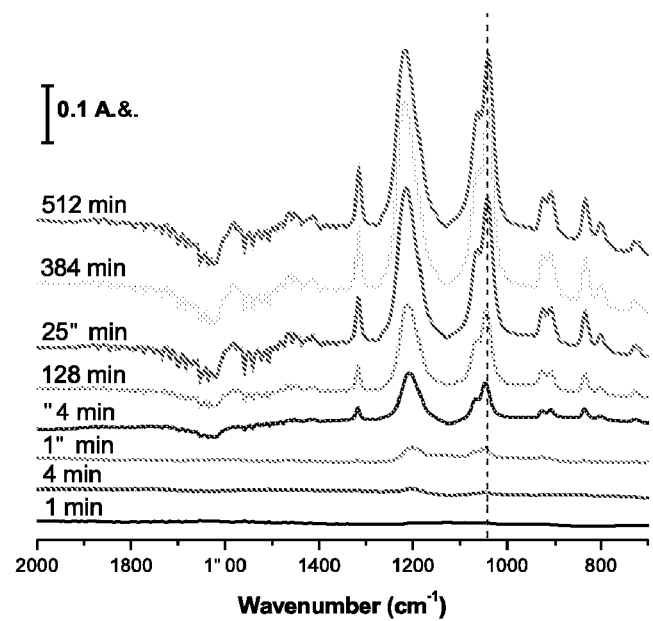
FIG. 12 is a graph of the reflectance absorption spectra obtained from the thickest ZnS coated Au/Ti/glass substrate (3 mg/cm$^2$) exposed to nitrogen stream (2 L/min) containing 50 ppt of DMMP for total of 1, 4, 16, 64, 128, 256, 384 and 512 minutes.

The reflectance absorption spectra obtained from the thickest ZnS coated Au/Ti/glass substrate (3 mg/cm$^2$) exposed to nitrogen stream (2 L/min) containing 50 ppt of DMMP for total of 1, 4, 16, 64, 128, 256, 384 and 512 minutes are presented in FIG. 12. The set of spectra collected with the thickest coating of ZnS is similar to the other sets of spectra obtained with thinner coatings of ZnS after exposure to DMMP. All of the ZnS coated substrates tested showed increase in the absorbance bands corresponding to DMMP with exposure time at the beginning. However, they reach the saturation point after different length of exposure to DMMP.

Figure 13:
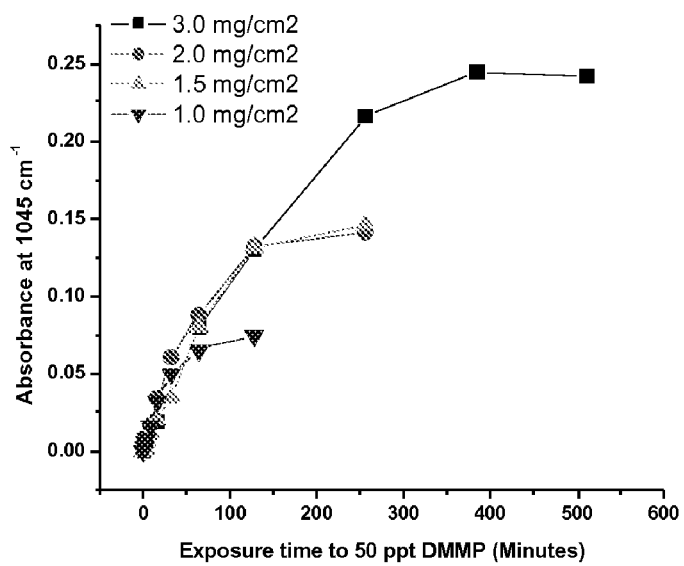
FIG. 13 is a graph of absorbance at 1042 cm$^{-1}$ ($v$ P=O) measured from sets of spectra presented in FIG. 12 against the exposure time to 50 ppt DMMP.

Plots of absorbance at 1042 cm$^{-1}$ (v P=O) measured from sets of spectra presented in FIG. 12 against the exposure time to 50 ppt DMMP are similar for short exposure (up to 30 minutes) to DMMP vapors, and also show a linear increase in response with the exposure time. However, upon prolonged exposure to DMMP the substrates get saturated at different points as presented in FIG. 13. As expected the substrate with the thinnest coating (1 mg ZnS/cm$^2$) show saturation after about an hour of exposure to 2 L/min flow of 50 ppt DMMP. Both the substrates with 1.5 mg/cm2 and 2.0 mg ZnS/cm$^2$ showed saturation after about 2 hours, and the thickest coating tested with 3 mg ZnS/cm$^2$ show saturation after about 4 hours.

These results indicate that the DMMP vapor coming in contact with the ZnS coating is quantitatively captured by the coating until it is saturated. This implies that the IR response is limited by the amount of DMMP introduced into the system, and not by the adsorbent coating or the air sampling system. The extended linear response range in case of the thicker coatings also indicates DMMP vapors can rapidly diffuse into the bulk of the ZnS coatings, and the adsorption of DMMP is not limited to the outer layer of the ZnS coatings.

Example 16

Detection of Chemical Agents in Continuous Sample Flow

A system was prepared by integrating the sample holder/air sampler and the front-end assembly (optical interface), a Bruker Tensor 27 FTIR spectrophotometer and controlled vapor generation and blending system. The controlled vapor generation and blending system consists of mass flow controllers (MFCs) and a bubbler and a long temperature equilibration stainless steel tubing immersed in a temperature controlled bath. First MFC flows high purity nitrogen gas through a sparger and into the chemical at a very low flow rate. The chemical is submerged in a temperature controlled bath in order to control the temperature. The second MFC then further dilutes the gas mixture with a much higher flow of high purity nitrogen. This gas mixture is then channeled through a static mixer in order to get a homogenous gas mixture. The gas then flows through the gas sampler and then vented to a fume hood. This integrated system allows for collection of multiple spectra without taking the substrate in and out of the sample holder and also during the exposure to the test air stream.

Gold on titanium on glass substrates with only a spot (~6 mm) of zinc sulfide were prepared by first stamping a circular pattern with a polydimethylsiloxane (PDMS) stamp wetted with 0.1 M sodium sulfide solution followed by deposition of 15 µL of 3% zinc sulfide slurry in water. The substrate was allowed to stand overnight, and baked in an oven at 200° C. for 4 hours to remove water completely. Such substrates are expected to provide stronger signal compared to the fully covered substrates used previously, as a larger fraction of the analyte adsorbed is interrogated by IR.

Figure 14:
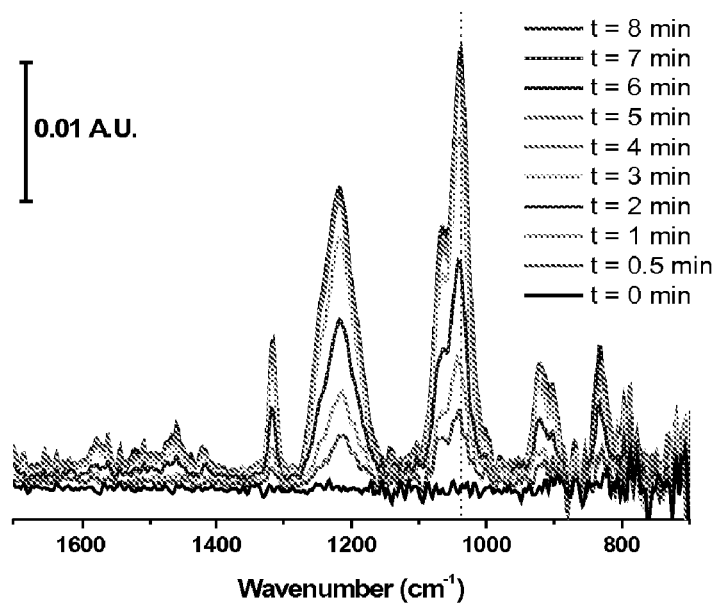
FIG. 14 is a graph of reflectance absorption spectra collected at various times before and after exposure to 2 L/min flow of nitrogen containing 50 ppt DMMP 4.

Using this set up and the newly prepared spot of ZnS on Au/Ti/Glass substrate, 50 ppt of DMMP could be detected in less than a minute. FTIR spectra collected before and after exposure to 2 L/min flow of nitrogen containing 50 ppt DMMP are presented in FIG. 14. The spectra presented in the figure are average of only 16 scans. The reference spectrum, and the spectrum at t=0 min were collected with 2 L/min of nitrogen flowing through the system, while rest of the spectra were collected with 2 L/min flow of nitrogen with 50 ppt DMMP. The characteristic absorption bands for DMMP could be clearly seen even after 30 sec exposure.

Figure 15:
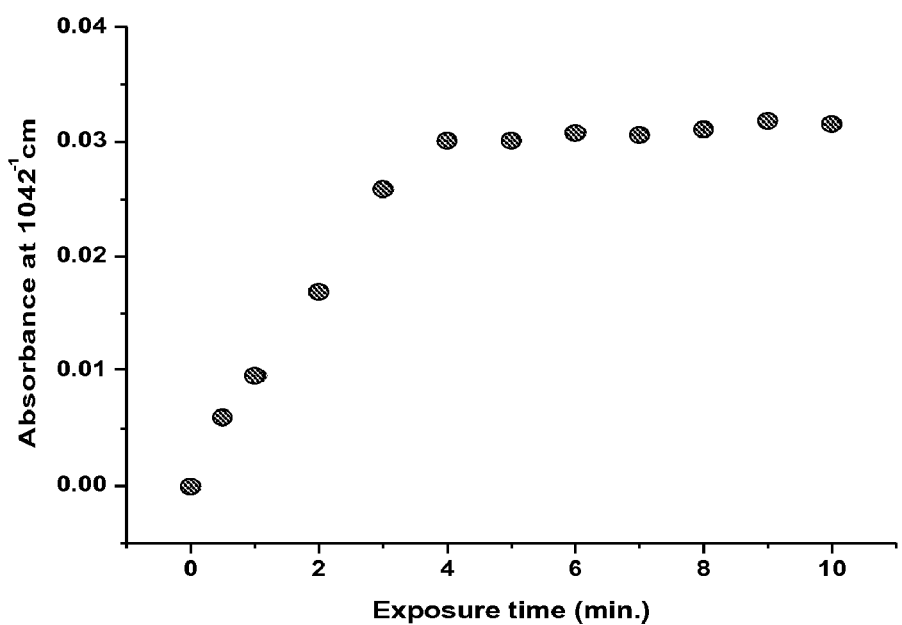
FIG. 15 is a graph of absorbance at 1042 cm$^{-1}$ ($v$ P=O) measured from the set of spectra against the exposure time to 50 ppt DMMP.

A graph of absorbance at 1042 $cm^{-1}$ (v P=O) measured from the set of spectra against the exposure time to 50 ppt DMMP as presented in FIG. 15, show a linear increase in IR response with the exposure time up to 4 minutes and then level off, indicating the saturation of the substrate, or reaching of an equilibrium state. It is known from previous studies of such substrates with various thicknesses of zinc sulfide that the saturation point is a function of the amount of zinc sulfide present in the substrate. Therefore, a thicker layer of zinc sulfide substrate can be used for an increased dynamic range.

These results demonstrate major improvements in the detection speed and spectral qualities (significantly improved baseline) compared to previous method of exposing the substrate to DMMP in an air sampler not integrate with the FTIR spectrometer.

Example 17

Detection of Explosives (DNT)

Figure 16:
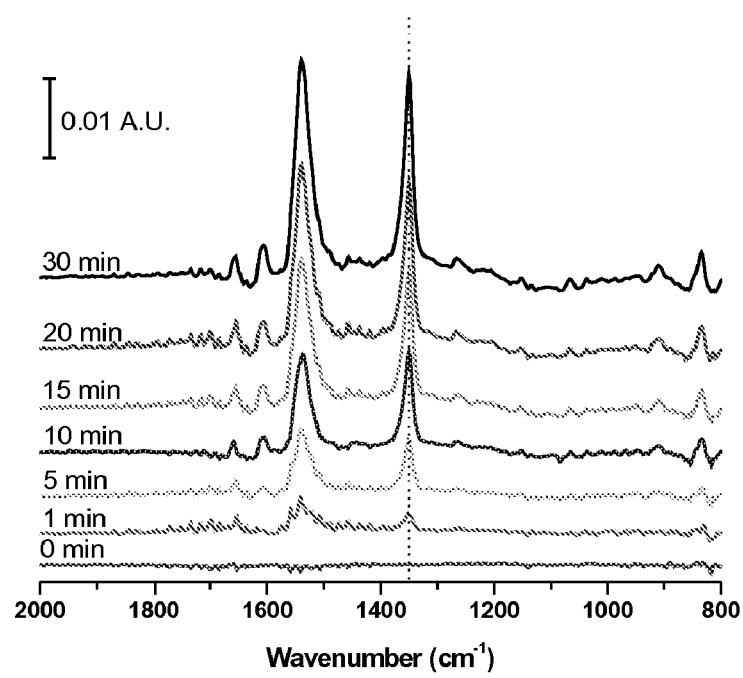
FIG. 16 is a graph of reflectance absorption spectra collected after 1, 5, 10, 15, 20 and 30 minute exposure to a 12 L/min flow of 20 ppb DNT in air.
Figure 17:
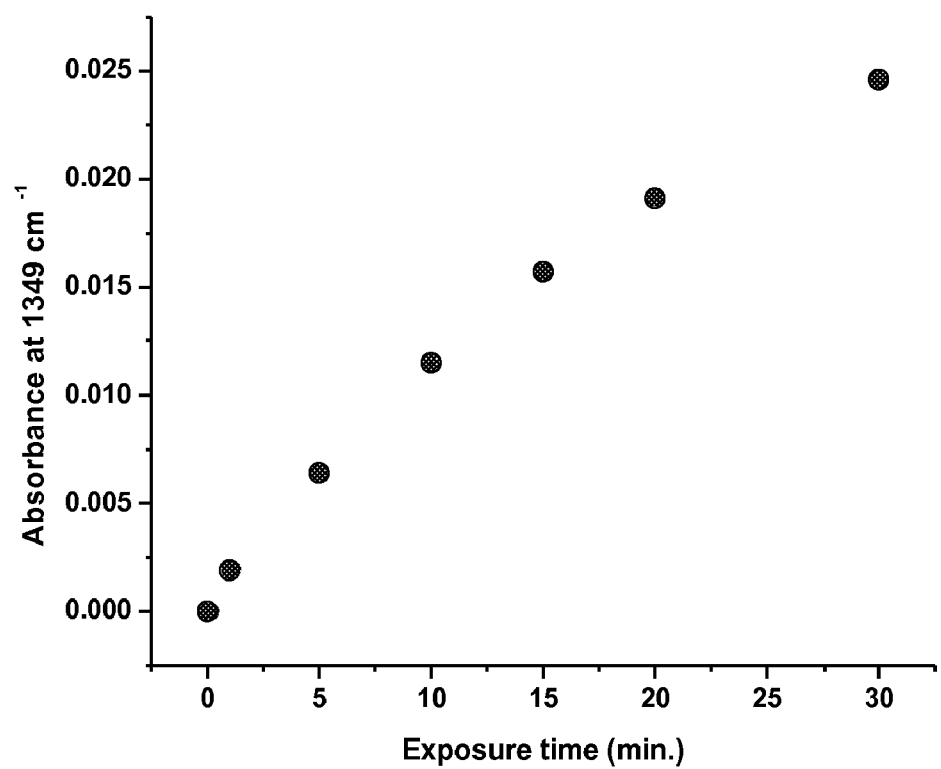
FIG. 17 is a graph of absorbance at 1349 cm$^{-1}$ ($v_s$ —NO$_2$) measured from the set of spectra against the exposure time to 20 ppb DNT showing increase in IR response with the increase in exposure time.

Using ZnS coated Au/Ti/Glass substrate and a set up same as in Part 3a, 20 ppb of 2,4-dinitro toluene (DNT) has also been detected in air after flowing a 12 L/min air flow containing 20 ppb DNT for 1 minute through the system. FIG. 16 is a graph of reflectance absorption spectra collected after 1, 5, 10, 15, 20 and 30 minute exposure to a 12 L/min flow of 20 ppb DNT. FIG. 17 is a graph of absorbance at 1349 $cm^{-1}$ ($v_s$ —$NO_2$) measured from the set of spectra against the exposure time to 20 ppb DNT show increase in IR response with the increase in exposure time.

The following terms shall be given the meanings setout hereinbelow. The term "mesoporous" means that a material has pores with a diameter between about 2 nanometers and about 50 nanometers. However, referring to a material as being mesoporous does not preclude the presence of a minor amount of microporosity (pores having less than about 2 nanometer diameter) or macroporosity (pores having greater than about 50 nanometer diameter). A "nanocomposite" means a material that is a composite on the scale of nanometers. "Spectroscopy," and other forms of the word such as "spectroscopic," refer to the study of the dependence of physical quantities on frequency. A "spectroscopic response" is the amount or intensity of a spectrum being absorbed or emitted as the result of imparting a particular stimulation on at least one analyte of interest.

The terms "comprising," "including," and "having," as used in the claims and specification herein, shall be considered as indicating an open group that may include other elements not specified. The term "consisting essentially of," as used in the claims and specification herein, shall be considered as indicating a partially open group that may include other elements not specified, so long as those other elements do not materially alter the basic and novel characteristics of the claimed invention. The terms "a," "an," and the singular forms of words shall be taken to include the plural form of the same words, such that the terms mean that one or more of something is provided. For example, the phrase "a solution comprising a hydrocarbon-containing compound" should be read to describe a solution having one or more hydrocarbon-containing compound. The term "one" or "single" shall be used to indicate that one and only one of something is intended. Similarly, other specific integer values, such as "two," are used when a specific number of things is intended. The terms "preferably," "preferred," "prefer," "optionally," "may," and similar terms are used to indicate that an item, condition or step being referred to is an optional (not required) feature of the invention.

It should be understood from the foregoing description that various modifications and changes may be made in the preferred embodiments of the present invention without departing from its true spirit. It is intended that this foregoing description is for purposes of illustration only and should not be construed in a limiting sense. Only the language of the following claims should limit the scope of this invention.

What is claimed is:

1. A method, comprising:
 exposing a solid material to a mixed fluid stream containing at least one analyte, wherein the solid material is substantially spectroscopically transparent zinc sulfide having a surface area density that is greater than 100 square meters per gram, wherein the solid material is characterized by a vapor absorption capacity at least 100 times greater than the absorption capacity of bulk zinc sulfide;
 collecting the at least one analyte from a mixed fluid stream onto the solid material; and
 detecting the spectroscopic response of the at least one analyte collected on the surface.

2. A method, comprising:
 exposing a solid material to a mixed fluid stream containing at least one analyte, wherein the solid material is substantially spectroscopically transparent and has a surface area density that is greater than 100 square meters per gram, wherein the substantially spectroscopically transparent solid material is selected from zinc selenide and silver halides;
 collecting the at least one analyte from a mixed fluid stream onto the solid material; and
 detecting the spectroscopic response of the at least one analyte collected on the surface.

3. The method of claim 1, wherein the zinc sulfide solid material is substantially transparent at wavelengths ranging from 0.45 to 14 micrometers (22,000-750 $cm^{-1}$).

4. The method of claim 1, wherein the substantially spectroscopically transparent solid material is substantially infrared transparent, and wherein the spectroscopic response includes infrared spectra.

5. The method of claim 4, wherein the spectroscopic response is selected from transmission, diffuse and specular reflectance infrared spectroscopy, and attenuated total reflection infrared spectroscopy.

6. The method of claim 1, wherein the substantially spectroscopically transparent solid material is substantially ultraviolet-visible transparent, and wherein the spectroscopic response includes ultraviolet-visible spectra.

7. The method of claim 1, wherein the step of collecting includes preconcentrating the at least one analyte on the surface of the solid material.

8. The method of claim 1, further comprising:
 identifying the presence of an organic compound of interest in the at least one collected analyte, wherein the at least one collected analyte comprises a mixture of organic chemicals.

9. A method, comprising:
 exposing a surface of a solid material to a mixed fluid stream containing at least one analyte, wherein the solid material is substantially spectroscopically transparent and has a surface area density that is greater than 100 square meters per gram;
 collecting the at least one analyte from a mixed fluid stream onto the surface of the solid material; and
 detecting the spectroscopic response of the at least one analyte collected on the surface, wherein the solid material is zinc sulfide synthesized by reacting a zinc precursor compound and a sulfide compound.

10. The method of claim 9, wherein the zinc sulfide solid material is synthesized by reacting zinc chloride and sodium sulfide in the presence of a template compound.

11. The method of claim 10, wherein the template compound is an organic surfactant.

12. The method of claim 11, wherein the surfactant is selected the group consisting of cetyl trimethyl ammonium bromide and alkoxylate block polymers.

13. The method of claim 10, wherein the template is an alkoxylate block polymer.

14. The method of claim 10, further comprising:
 calcining the zinc sulfide to thermally decompose the template compound.

15. The method of claim 14, further comprising:
 acid washing the zinc sulfide to remove the thermally decomposed template composition.

16. The method of claim 10, further comprising:
 depositing at least one nanoparticulate metal species onto the zinc sulfide.

17. The method of claim 16, wherein the metal nanoparticles are selected from silver, gold, copper, platinum, palladium, iron, rhodium, and mixtures and alloys thereof.

18. The method of claim 16, wherein the metal nanoparticles are selected from gold, silver and copper.

19. The method of claim 18, characterized in that the gold, silver or copper nanoparticles provide an enhanced spectroscopic response.

20. The method of claim 19, wherein the nanoparticles provide a spectroscopic response characterized by an improved signal to noise ratio.

21. The method of claim 16, wherein the nanoparticulate metal is nanoparticulate gold prepared from hydrogen tetrachloroaurate.

22. The method of claim 16, wherein the step of depositing metal nanoparticles includes mixing the zinc sulfide with a colloidal solution of the metal nanoparticles to form a nanocomposite.

23. The method of claim 22, further comprising:
 washing and drying the nanocomposite of zinc sulfide and colloidal gold.

24. A method, comprising:
 mixing a solid material with an optically transparent binder and a solvent, wherein the solid material is substantially spectroscopically transparent and has a surface area density that is greater than 100 square meters per gram;
 applying the mixture onto the surface of a substrate;
 removing the solvent;
 exposing the solid material to a mixed fluid stream containing at least one analyte;
 collecting the at least one analyte from a mixed fluid stream onto the solid material; and
 detecting the spectroscopic response of the at least one analyte collected on the surface, wherein the steps of mixing the solids with a binder, applying the mixture onto the surface, and removing the solvent occur prior to exposing the solid material to the mixed fluid stream.

25. The method of claim 24, wherein the binder is polytetrafluoroethylene.

26. A method, comprising:
 forming a coating with 1 nanogram/cm$^2$ to 10 mg/cm$^2$ of spectroscopically transparent zinc sulfide on a gold metal surface of a solid substrate, wherein the zinc sulfide has a surface area density that is greater than 100 square meters per gram; and then
 exposing the coated substrate to a mixed fluid stream containing at least one analyte;
 collecting the at least one analyte from the mixed fluid stream onto the coated substrate; and
 detecting the spectroscopic response of the at least one analyte collected on the coated substrate.

27. The method of claim 26, where the coating is applied over less than 1 cm$^2$ of the solid substrate to concentrate the analyte for detecting the spectroscopic response.

28. The method of claim 2, wherein the step of collecting includes preconcentrating the at least one analyte on the surface of the solid material.

29. The method of claim 2, further comprising:
 identifying the presence of an organic compound of interest in the at least one collected analyte, wherein the at least one collected analyte comprises a mixture of organic chemicals.

30. The method of claim 2, further comprising:
 mixing the solid material with an optically transparent binder and a solvent;
 applying the mixture onto the surface of a substrate; and
 removing the solvent, wherein the steps of mixing the solids with a binder, applying the mixture onto the surface, and removing the solvent occur prior to exposing the solid material to the mixed fluid stream.

* * * * *

UNITED STATES PATENT AND TRADEMARK OFFICE
CERTIFICATE OF CORRECTION

| | | |
|---|---|---|
| PATENT NO. | : 7,808,632 B2 | Page 1 of 1 |
| APPLICATION NO. | : 11/768040 | |
| DATED | : October 5, 2010 | |
| INVENTOR(S) | : Bikas Vaidya and Ulf Werner Drechsler | |

It is certified that error appears in the above-identified patent and that said Letters Patent is hereby corrected as shown below:

Column 1, line 4 below the Title please insert the following:

--This invention was made with government support under contract number W911SR-04-P-0084 awarded by the Department of Defense (Army). The government has certain rights in this invention.--

Signed and Sealed this
Fourth Day of January, 2011

David J. Kappos
*Director of the United States Patent and Trademark Office*